(12) United States Patent
Zilles et al.

(10) Patent No.: US 9,035,042 B2
(45) Date of Patent: *May 19, 2015

(54) SULFONAMIDE DERIVATIVES OF POLYCYCLIC DYES USED FOR ANALYTICAL APPLICATIONS

(75) Inventors: Alexander Zilles, Netphen (DE); Jutta Arden-Jacob, Zirndorf (DE); Karl-Heinz Drexhage, Siegen (DE); Norbert Uwe Kemnitzer, Netphen (DE); Monika Hamers-Schneider, Freudenberg (DE)

(73) Assignee: ATTO-TEC GmbH, Siegen (DE)

( * ) Notice: Subject to any disclaimer, the term of this patent is extended or adjusted under 35 U.S.C. 154(b) by 896 days.

This patent is subject to a terminal disclaimer.

(21) Appl. No.: 10/563,079

(22) PCT Filed: Jul. 2, 2004

(86) PCT No.: PCT/EP2004/007248

§ 371 (c)(1),
(2), (4) Date: Dec. 30, 2005

(87) PCT Pub. No.: WO2005/003086

PCT Pub. Date: Jan. 13, 2005

(65) Prior Publication Data

US 2006/0179585 A1 Aug. 17, 2006

(30) Foreign Application Priority Data

Jul. 2, 2003 (DE) .................. 103 29 860

(51) Int. Cl.
| | | |
|---|---|---|
| *A61K 8/00* | (2006.01) | |
| *C07D 401/12* | (2006.01) | |
| *C07D 215/12* | (2006.01) | |
| *C07D 215/14* | (2006.01) | |
| *C07D 215/20* | (2006.01) | |
| *C07D 215/38* | (2006.01) | |
| *C07D 221/18* | (2006.01) | |
| *C07D 405/12* | (2006.01) | |
| *C07D 413/12* | (2006.01) | |
| *C07D 471/04* | (2006.01) | |
| *C07D 491/04* | (2006.01) | |
| *C07D 491/14* | (2006.01) | |
| *C07D 491/22* | (2006.01) | |
| *C07D 498/04* | (2006.01) | |
| *C07D 498/14* | (2006.01) | |

(52) U.S. Cl.
CPC ............ *C07D 401/12* (2013.01); *C07D 215/12* (2013.01); *C07D 215/14* (2013.01); *C07D 215/20* (2013.01); *C07D 215/38* (2013.01); *C07D 221/18* (2013.01); *C07D 405/12* (2013.01); *C07D 413/12* (2013.01); *C07D 471/04* (2013.01); *C07D 491/04* (2013.01); *C07D 491/14* (2013.01); *C07D 491/22* (2013.01); *C07D 498/04* (2013.01); *C07D 498/14* (2013.01)

(58) Field of Classification Search
CPC .. C07D 401/12; C07D 215/12; C07D 215/14; C07D 215/20; C07D 215/38; C07D 221/18; C07D 405/12; C07D 413/12; C07D 471/04; C07D 491/14; C07D 491/22; C07D 498/04
USPC ............ 536/54; 540/467; 546/48, 57, 77, 89; 544/99

See application file for complete search history.

(56) References Cited

U.S. PATENT DOCUMENTS

| | | | |
|---|---|---|---|
| 5,750,409 A | 5/1998 | Herrmann et al. ............ 436/517 |
| 6,013,531 A * | 1/2000 | Wang et al. .................. 436/526 |
| 6,130,101 A | 10/2000 | Mao et al. ..................... 436/546 |
| 6,184,379 B1 * | 2/2001 | Josel et al. ...................... 546/48 |
| 6,221,600 B1 | 4/2001 | MacLeod et al. ............. 435/6.1 |
| 6,664,110 B1 * | 12/2003 | Tsuji et al. ...................... 436/63 |
| 6,716,979 B2 * | 4/2004 | Diwu et al. ..................... 544/99 |
| 6,737,280 B1 | 5/2004 | Drexhage et al. ............. 436/546 |
| 6,828,159 B1 * | 12/2004 | Drexhage et al. ............. 436/546 |
| 7,294,487 B2 * | 11/2007 | MacLeod et al. ............ 435/91.2 |
| 2003/0027141 A1* | 2/2003 | MacLeod et al. ................ 435/6 |

FOREIGN PATENT DOCUMENTS

| | | |
|---|---|---|
| EP | 0 567 622 B1 | 11/1992 |
| EP | 0 747 447 B1 | 5/1995 |
| GB | 2 044 258 | 10/1980 |
| GB | 2 054 582 | 2/1981 |
| GB | 2 148 917 A | 6/1985 |
| GB | 2 148 918 A | 6/1985 |
| GB | 2 148 919 A | 6/1985 |
| GB | 2 148 920 | 6/1985 |
| HU | 188 100 | 3/1985 |
| WO | WO 87/00048 | 1/1987 |
| WO | WO 88/08420 | 11/1988 |
| WO | WO 92/07833 | 5/1992 |
| WO | WO 99/15517 | 4/1999 |
| WO | WO 00/64987 | 11/2000 |
| WO | WO 0064986 | 11/2000 |
| WO | WO 02/099077 A2 | 12/2002 |

OTHER PUBLICATIONS

Burroughs-tencza, Sarah (AN 2001:598212, HCAPLUS, abstract WO 2001059149).*
MacLeod, Michael et al. (AN 2001:284151, HCAPLUS abstract WO 2001027329).*

(Continued)

*Primary Examiner* — Sabiha N Qazi
(74) *Attorney, Agent, or Firm* — Henry M. Feiereisen LLC; Ursula B. Day

(57) ABSTRACT

The invention concerns the production of quinoline compounds containing sulfonic acid groups, the said quinoline compounds and their conversion into dyes containing sulfonic acid groups. The dyes according to the invention are used especially to label analytes, for example to label biomolecules.

6 Claims, No Drawings

(56) References Cited

OTHER PUBLICATIONS

Panchuk-Voloshina et al. (AN 1999:602622, HCAPLUS abstract J. of Histochemistry and Cytochemistry (1999), 47(9), 1179-1188).*

XP-002360495, Alexa Dyes, a Series of New Fluorescent Dyes that Yield Exceptionally Bright, Photostable Conjugates by Nataliya Panchuk-Voloshina et al./ *Journal of Histochemistry & Cytochemistry*; vol. 47(9):11794-1188. 1999.

Flourescent Probes in Cellular and Molecular Biology by Jan Slavik,PhD, *CRC Press, Inc.,Boca Raton/ 1994 (Institute of Physiology Czech Academy of Sciences)*.

Jan Slavik,Ph.D.: "Fluorescent Probes in Cellular and Molecular Biology", CRC Press, Boca Raton, Ann Arbor, London, Tokyo, 1994.

* cited by examiner

SULFONAMIDE DERIVATIVES OF POLYCYCLIC DYES USED FOR ANALYTICAL APPLICATIONS

BACKGROUND OF THE INVENTION

The invention concerns the production of quinoline compounds containing sulfonic acid groups, said quinoline compounds and the conversion thereof into dyes containing sulfonic acid groups. The dyes according to the invention can be used especially to label analytes and for example to label biomolecules.

Dyes from the class of coumarin, xanthene and oxazine dyes and related derivatives are preferably used as labelling groups in chemical, biological and medical analytics due to their very good spectral properties and in particular their fluorescence. (J. Slavik, Fluorescent probes in Cellular and Molecular Biology, CRC Press, Boca Raton, Ann Arbor, London, Tokyo, 1994). A large number of long wavelength xanthene dyes (rhodamines etc.) are described in EP 0567622 B1. Labelling dyes from the oxazine class are disclosed in EP 0747447 B1. Sulfonic acid derivatives of xanthene dyes are described in WO 99/15517. Dyes from the carbopyronine and amidopyrylium dye classes are described in WO 00/64986 and WO 00/64987. In this connection dyes having a high fluorescence quantum yield play an important role since the fluorescence enables a very sensitive detection of the labelled analyte. However, non-fluorescent derivatives are becoming increasingly important as quenchers in special methods.

A good solubility e.g. in aqueous systems is necessary in addition to a simple and reliable detectability for an application as labelling groups for analytes. In other cases exactly the opposite is desired i.e. a good solubility in an unpolar environment e.g. cell membranes.

Hence, depending on the concrete conditions, certain specific properties which the fluorophore should have in addition to its optical properties are of decisive importance for an application as a labelling group for analytes or in similar methods. In the case of the dyes of the said patents, these properties can either not be achieved or, if at all, only in a very complicated manner by dye synthesis using appropriate educts.

Hence an object of the present invention was to simply and also subsequently modify certain physical and/or chemical properties of these dyes such as their solubility in certain media, their tendency to interact unspecifically with substrates and/or vessel walls or their coupling ability without essentially changing the very good spectral properties of the dyes.

SUMMARY OF THE INVENTION

This object is achieved according to the invention by the preparation of compounds of the general formulae Ia and Ib

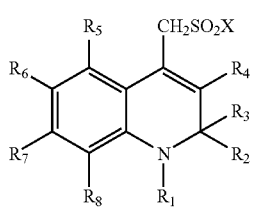

Ia

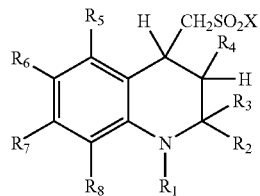

Ib

As well as their use for preparing dyes which can for example be used as labelling groups in a method for detecting analytes in which $R_1$ denotes hydrogen or a saturated or unsaturated, straight-chained, branched or cyclic hydrocarbon group with up to 20 C atoms e.g. polyether, phenyl, phenylalkyl with 1-3 C atoms in the chain, where the hydrocarbon groups can optionally contain heteroatoms such as oxygen, sulfur or nitrogen atoms or/and one or more substituents preferably selected from halogens, hydroxy, amino, sulfo, phospho, carboxy, carbonyl, alkoxy or/and alkoxycarbonyl groups, $R_2$, $R_3$, $R_4$, $R_5$, $R_6$, $R_7$ and $R_8$ each independently denote hydrogen, halogen, a hydroxy, amino, sulfo or carboxy or aldehyde group or a saturated or unsaturated, straight-chained, branched or cyclic hydrocarbon group with up to 20 C atoms where the hydrocarbon groups comprise alkyl, alkenyl, alkinyl, cycloalkyl, aryl, in particular phenyl or/and heteroaryl residues and can optionally also contain heteroatoms such as oxygen, sulfur or nitrogen atoms or/and several substituents preferably selected from halogens, hydroxy, amino, phospho, sulfo, carboxy, carbonyl, alkoxy or/and alkoxycarbonyl groups, or the residue $R_8$ forms a ring system with $R_1$ which can contain one or more multiple bonds and X denotes halogen, a hydroxy, alkoxy, alkylthio or amino group, where the hydrocarbon residues that may be present in these groups comprise in particular alkyl, alkenyl, alkinyl, cycloalkyl, aryl, in particular phenyl or/and heteroaryl residues and can optionally also contain heteroatoms such as oxygen, sulfur or nitrogen atoms or/and several substituents preferably selected from halogens, hydroxy, amino, phospho, sulfo, carboxy, carbonyl, alkoxy or/and alkoxycarbonyl groups.

In preferred embodiments $R_1$ denotes an aryl or alkyl residue, $R_2$ and $R_3$ each denote methyl and $R_4$ denotes hydrogen.

In other particularly preferred embodiments $R_1$ denotes an aryl or alkyl residue, $R_2$ and $R_3$ each denote methyl, $R_4$ denotes hydrogen and $R_7$ denotes a hydroxy or methoxy group.

In additional particularly preferred embodiments $R_1$ denotes an aryl or alkyl residue, $R_2$ and $R_3$ each denote methyl, $R_4$ denotes hydrogen and $R_6$ denotes a nitroso, formyl or a hydroxymethyl group.

In a further particularly preferred class of compounds $R_1$ is bridged with $R_8$ to form a ring system and in particular a 5-membered or 6-membered ring.

The dyes that are preferably used or prepared are representatives of the classes compiled in the following of the general formulae II to VII but are not limited to these classes. In the case of dyes of the classes III and V to VII which have a symmetric chromophoric system, it is possible according to the invention to introduce two equal or different $SO_2X$ groups by selection of the educts. It is possible to produce corresponding dyes having tetrahydroquinoline end groups in the same manner as for the educts I by means of subsequent hydrogenation.

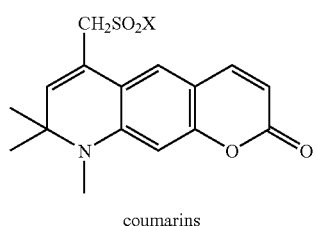

coumarins

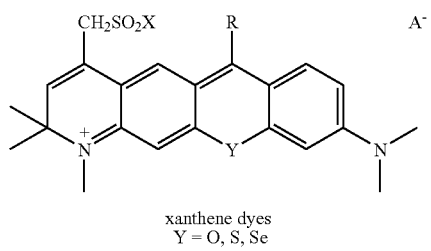

xanthene dyes
Y = O, S, Se

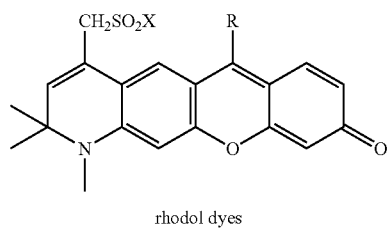

rhodol dyes

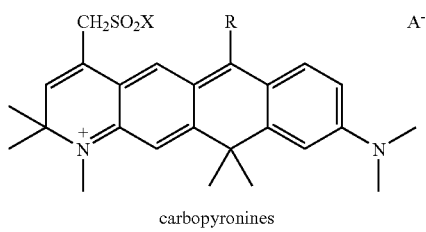

carbopyronines

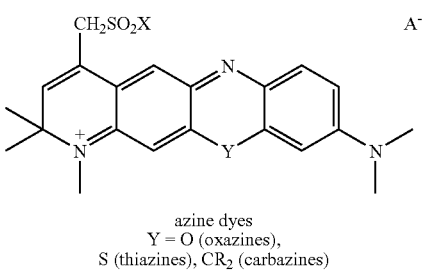

azine dyes
Y = O (oxazines),
S (thiazines), CR₂ (carbazines)

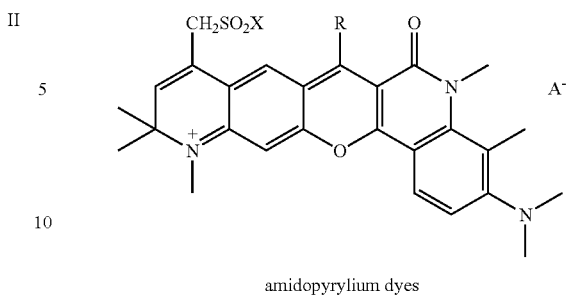

amidopyrylium dyes in which R is in particular H, (subst.) aryl, (subst.) carboxyphenyl, (subst.) alkyl, (subst.) cycloalkyl, (subst.) pyridyl, (subst.) carboxypyridyl etc. According to the invention it is possible either to sulfonate appropriate precursors of the synthesis or sulfonate the actual dyes and subsequently derivatize the sulfonic acid group(s). For this purpose the sulfonic acid or its salt are preferably converted into a sulfochloride which is subsequently reacted with a nucleophile (e.g. amino or mercapto group). The sulfonation succeeds for example in concentrated sulfuric acid optionally in a mixture with oleum. The sulfonic acid derivatives of both the precursors and the dyes can be reacted in a simple manner with phosphoroxy chloride, phosphorus pentachloride or thionyl chloride preferably in a mixture with dimethylformamide to form a sulfochloride. Surprisingly it was possible to isolate the sulfochlorides in almost all cases without problems. The sulfochlorides react with various nucleophiles, preferably with primary or secondary amines to form corresponding sulfonamide derivatives. The physical and/or chemical properties of the compounds obtained in this manner also depend very decisively on the properties of the amine that is used which is elucidated later in more detail also on the basis of examples. An astonishingly large diversity of pH-stable sulfonamide derivatives is obtained in this process. The type of sulfonamide linkage according to the invention ensures a spatial separation of substituent and chromophore thus preventing a disadvantageous effect on the fluorescence efficiency. The dye sulfochlorides can also be used directly without prior derivatization for coupling to nucleophilic ($NH_2$ etc. groups) groups of analyte molecules.

The term heteroatoms as used herein comprises in particular oxygen, sulfur and nitrogen atoms.

If not stated otherwise, the term substituents comprises in particular halogen, hydroxy, amino, sulfo, phospho, carboxy, alkoxy as well as alkoxycarbonyl groups with, if present, 1-10 C atoms.

The following general processes are used to prepare the compounds according to the invention. It is possible to derivatize either the precursors (section 1) or the finished dyes (section 2).

1. Synthesis of Appropriate Precursors

Starting with a 7-alkoxy-2,2,4-trimethyl-1,2-dihydroquinoline prepared according to methods known in the literature e.g. by condensing an aniline derivative with mesityl oxide and subsequent N-alkylation, the inventive procedure is as follows:

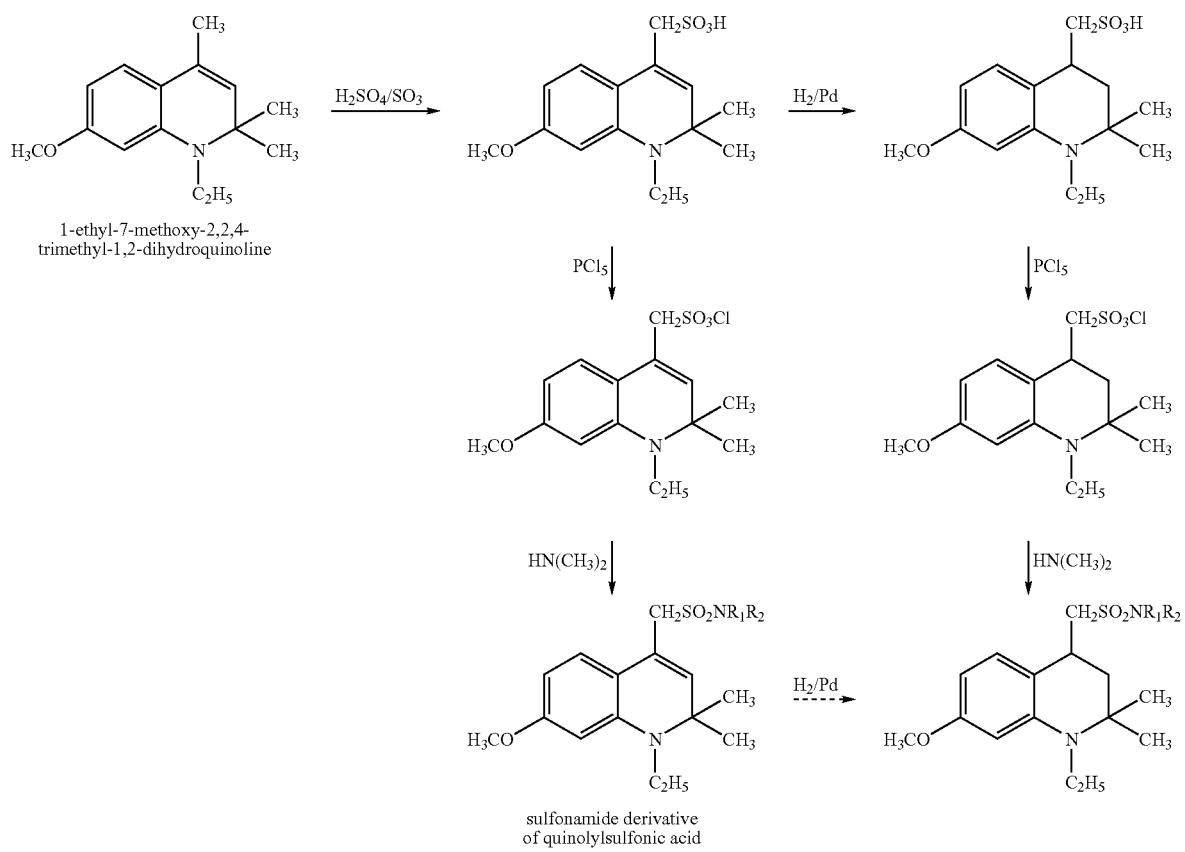

Figure 1:

Examples of the preparation of compounds according to the invention. Starting from 1-ethyl-7-methoxy-2,2,4-trimethyl-1,2-dihydroquinoline, a sulfonamide derivative is finally obtained via the sulfonic acid and sulfochloride intermediate stages. The corresponding 1,2,3,4-tetrahydroquinoline derivative can be obtained by intermediate hydrogenation.

A product sulfonated on the 4-methyl group is obtained by stirring the dihydro-quinoline with a mixture of concentrated sulfuric acid and oleum at room temperature. This sulfonic acid or its salt can be readily converted into the sulfochloride. For this the sulfonated compound is reacted in benzene with phosphorus pentachloride preferably at room temperature. In general common reagents such as phosphoroxy chloride, phosphorus pentachloride or thionyl chloride are used to prepare the sulfochloride. The reaction is carried out in an anhydrous inert solvent, preferably benzene.

The sulfochloride can be converted into a corresponding sulfonamide by simple reaction with almost any primary and secondary amines. The sulfochloride can also react with other nucleophiles (thiols, alcohols etc.). If necessary the stable sulfonamide that is obtained can be further derivatized (saponification of carbonic ester groups etc.).

The 1,2-dihydroquinoline can for example at the sulfonic acid stage be hydrogenated with hydrogen which is catalysed by palladium and thus be converted into a 1,2,3,4-tetrahydroquinoline. This hydrogenated quinoline can subsequently be subjected to the same synthetic pathway (see Figure 1).

The following dye syntheses are carried out by preparation methods known to a person skilled in the art using the sulfonic acids, their salts or preferably the sulfonamide derivatives that are obtained in this manner:

Symmetric rhodamine dyes can for example be obtained by condensation of the described sulfonamide derivative with phthalic anhydride. Other xanthene dyes such as trifluoromethyl, pyronine or rosamine dyes are obtained by condensation with the appropriate acid anhydrides (trifluoroacetic anhydride) or aldehydes (benzaldehyde etc.).

Asymmetric dyes are obtained in the case of rhodamines by for example reacting phthalic anhydride with an aminophenol or hydrogenated 7-hydroxy-quinoline or 7-methoxyquinoline and subsequently reacting the benzophenone derivative that is formed for example with a second dihydroquinoline or tetrahydroquinoline whereby a sulfonamide derivative according to the invention can now for example be used.

Representatives of other dye classes such as coumarins, carbopyronines, amido-pyrylium dyes, oxazines etc. can be produced by methods known in the literature using the sulfonic acids, salts thereof or the sulfonamide derivates of the afore-mentioned or similar quinoline precursors. This means that the compounds according to the invention can be surprisingly used without problems in the known synthetic processes for preparing the dyes.

2. Subsequent Derivatization of the Dyes

According to the invention dyes can be subsequently sulfonated on their 4-methyl group. A similar process is described in the patent application WO 99/15517 for xanthene dyes. Surprisingly such a subsequent sulfonation also succeeds in the case of many other polycyclic dyes which considerably simplifies the synthesis of the sulfonamide derivatives according to the invention.

The sulfonated dyes obtained in this manner can surprisingly be converted into sulfochlorides as described above for the educts without changing or destroying the chromophore in this process. In this case apart from phosphoroxy chloride and/or phosphorus pentachloride, it is preferable to use a mixture of thionyl chloride and dimethylformamide. The sulfochlorides can be isolated and purified as perchlorates. The isolated dye sulfochlorides can be used in a known manner directly as markers for amino groups in biomolecules. However, the sulfochlorides obtained in this manner can be reacted with almost any primary and secondary amines as described above for the quinoline precursors. This allows the dyes according to the invention to be obtained in a particularly simple manner.

The introduction of the sulfonic acid group and its derivatization has almost no effect on the spectral properties of the dyes such as absorption and fluorescence maximum, extinction coefficient and the fluorescence quantum yield.

However, the described process allows one to impart a large variety of new properties to the dyes in a simple manner or even subsequently depending on the primary or secondary amine that is used. This is because the amine can carry almost any additional functional groups. Thus for example our process allows one to introduce cyano, mercapto, halogen, sulfonic acid, hydroxy, alkenyl groups etc. into the dye.

If the amine that is used carries relatively long alkyl chains e.g. $C_{10}$ to $C_{30}$, this increases the lipophilic character and the compound is soluble in unpolar media and membranes and can be used to detect membrane properties or to measure molecular distances.

The water solubility of a dye can be improved when the amine in turn carries sulfonic acid or phosphonic acid groups or has polyether chains. The latter also improve the solubility of the compound in many organic solvents. They also reduce undesired unspecific interactions with the substrate or vessel walls. The crown ethers used for a sensitive fluorescence-based detection of cations are a type of cyclic polyether which can also be coupled as aza derivatives to dye molecules using the method described here. Furthermore the described method also allows the preparation of bichromophoric systems in which energy transfer (FRET) takes place between the chromophores.

If the amine carries substituents that are capable of covalent coupling e.g. —COOH, —NH$_2$, —OH or/and —SH, the compound produced according to the invention can be coupled by known methods to a carrier and/or to a biomolecule. Hence this procedure allows dyes to be used for labelling which do not themselves have a carboxyl group or such like that is capable of coupling as is still necessary for the sulfonic acid derivatives described in WO 99/15517. Any suitable material can be selected as a carrier e.g. porous glass, plastics, ion exchanger resins, dextrans, cellulose, cellulose derivatives or/and hydrophilic polymers. The biomolecules are preferably selected from peptides, polypeptides, nucleotides, nucleosides, nucleic acids, nucleic acid analogues or/and haptens.

A common method for covalently labelling biomolecules is the active ester method familiar to a person skilled in the art. Hence in a preferred manner a carboxylic acid with a terminal amino group and average chain length is used as the amine. Hence for example the commercial 4-methylaminobutyric acid, 4-piperidinecarboxylic acid, 6-aminohexanoic acid etc. can be used in an inventive manner as the amine. Thus after the sulfonamide linkage, dyes are obtained which have a carboxyl group that can be used for coupling. After coupling to primary amino groups of suitable biomolecules, the labelling group that is used and thus the analyte can be easily detected by means of its absorption and/or fluorescence.

The compounds that are obtained can be used as labelling groups and thus the analyte in methods for the qualitative or/and quantitative determination of an analyte. The determination can be carried out in aqueous liquids e.g. samples of body fluids such as blood, serum, plasma or urine, waste water samples or foods. The method can be carried out as a wet test e.g. in a cuvette or as a dry test on an appropriate reagent carrier. In this connection the analyte can be determined by a single reaction or by a sequence of reactions. The use of the compounds obtained shows very good results in chemical and in particular medical and biological detection methods for determining an analyte.

The compounds can be used in all known chemical, medical and biological detection methods in which fluorescent dyes are suitable as labelling groups. Such methods are known to a person skilled in the art and do not therefore have to be explained further.

In a particularly preferred embodiment the compound that is obtained is coupled covalently to a specific receptor for the analyte to be detected. The specific receptor is any suitable compound or any suitable molecule and it is preferably a peptide, polypeptide or a nucleic acid. The compounds or conjugates of these compounds can for example be used in nucleic acid hybridization methods or immunochemical methods. Such methods are described for example in Sambrook et al., Molecular Cloning, A Laboratory Manual, 1989, Cold Spring Harbor.

An important advantage of the described process is its unrestricted applicability to all dyes that can be synthesized using the dihydroquinolines and tetrahydro-quinolines described above. Hence the choice of chromophore allows one to exactly select the dyes which, due to their spectroscopic properties, the position of their absorption and fluorescence maxima, their solubility properties, their fluorescence decay time and the magnitude of the quantum yield, appear to be particularly suitable for the desired application.

As will be elucidated in the following examples, the compounds according to the invention can be produced by the methods described above in a simple and cost-effective manner. The compounds produced in this manner can be handled without problems and exhibit a good stability and shelflife.

Hence the invention especially concerns the production and use of dihydroquinoline and tetrahydroquinoline derivatives corresponding to formulae Ia and Ib where X=OH (sulfonic acids); X=Cl, Br, I (sulfonylhalogenides, preferably chlorides); X=NR$_1$R$_2$ where R$_1$ and R$_2$=substituted alkyl, aryl etc. (sulfonamides); X=OR or SR where R=alkyl, aryl etc. (sulfonic acid esters, thiosulfonic acid S esters) and the use of compounds corresponding to formulae Ia and Ib to produce polycyclic dyes corresponding to formulae II-VII.

The invention also comprises the production and use of polycyclic dyes corresponding to formulae II-VII by direct introduction of one or more substituents SO$_2$X into known dyes with dihydroquinoline or tetrahydroquinoline end groups except for X=OH in compounds corresponding to formula III in which Y=O and formula IV.

Dyes corresponding to formulae II-VII are preferably used to label analytes and in particular biomolecules (peptides, nucleotides etc.) via their NH$_2$ or SH groups.

The dyes corresponding to formulae II-VII in which X=Cl (sulfonyl chloride) can also be used for coupling with amino groups of an analyte.

The invention also comprises the use of dyes corresponding to formulae II-VII in which X=NR$_1$R$_2$ and R$_1$=COOH-substituted alkyl or aryl to form active esters (e.g. with N-hydroxysuccinimide) and subsequent couple them to the amino groups of an analyte. The dyes corresponding to formulae II-VII can also be used for coupling to free amino groups of other dyes (FRET pairs).

DETAILED DESCRIPTION OF PREFERRED EMBODIMENTS

Specific examples of compounds according to the invention are shown in tables 1 to 3.

TABLE 1
Quinolylsulfonic acids and derivatives thereof
| Example | Structure | Empirical formula | Mass MH+ |
|---------|-----------|-------------------|----------|
| 1 | 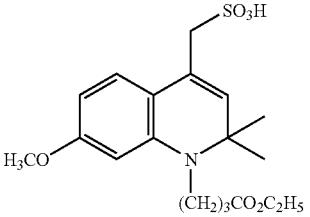 | $C_{19}H_{27}NO_6S$ | 398 |
| 2 | 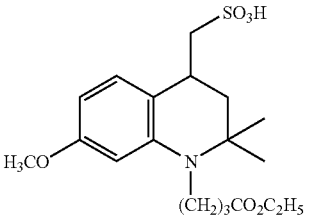 | $C_{19}H_{29}NO_6S$ | 400 |
| 3 | 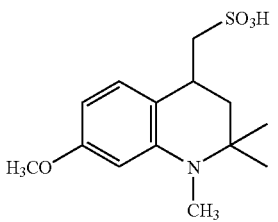 [SMILES: COc1ccc2c(c1)N(C)C(C)(C)CC2CS(=O)(=O)O] | $C_{14}H_{21}NO_4S$ | 300 |
| 4 | 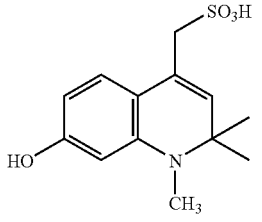 [SMILES: CN1c2cc(O)ccc2C(CS(=O)(=O)O)=CC1(C)C] | $C_{13}H_{19}NO_4S$ | 286 |
| 5 | 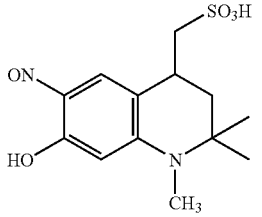 | $C_{13}H_{18}N_2O_5S$ | 315 |
| 6 | 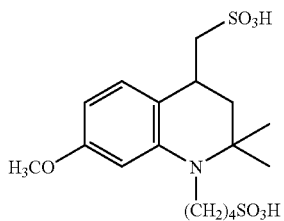 | $C_{17}H_{27}NO_7S_2$ | 421 |

TABLE 1-continued

Quinolylsulfonic acids and derivatives thereof

| Example | Structure | Empirical formula | Mass MH+ |
|---------|-----------|-------------------|----------|
| 7 | 7-methoxy-2,2-dimethyl-1,2,3,4-tetrahydroquinoline-4-methanesulfonic acid | $C_{13}H_{19}NO_4S$ | 286 |
| 8 | 1-ethyl-2,2-dimethyl-1,2-dihydroquinoline-4-methanesulfonic acid | $C_{14}H_{19}NO_3S$ | 284 |
| 9 | 1-ethyl-2,2-dimethyl-1,2-dihydroquinoline-4-methanesulfonyl chloride | $C_{14}H_{18}ClNO_2S$ | 302 |
| 10 | methyl 1-((1-ethyl-2,2-dimethyl-1,2-dihydroquinolin-4-yl)methylsulfonyl)piperidine-4-carboxylate | $C_{21}H_{30}N_2O_4S$ | 407 |
| 11 | N,N-diethyl-1-(1-ethyl-2,2-dimethyl-1,2-dihydroquinolin-4-yl)methanesulfonamide | $C_{18}H_{28}N_2O_2S$ | 337 |
| 12 | N-octyl-1-(1-ethyl-2,2-dimethyl-1,2-dihydroquinolin-4-yl)methanesulfonamide | $C_{22}H_{36}N_2O_2S$ | 393 |

TABLE 1-continued

Quinolylsulfonic acids and derivatives thereof

| Example | Structure | Empirical formula | Mass MH+ |
|---------|-----------|-------------------|----------|
| 13 | 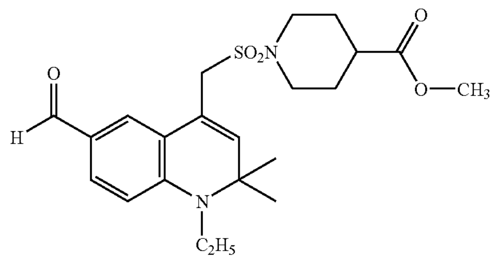 | $C_{22}H_{30}N_2O_5S$ | 435 |
| 14 | 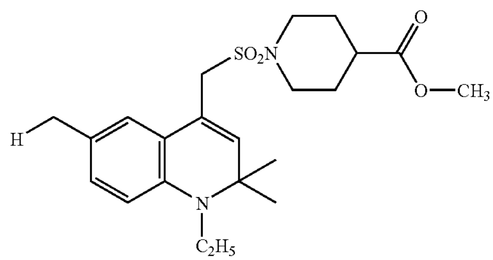 | $C_{22}H_{32}N_2O_5S$ | 437 |
| 15 | 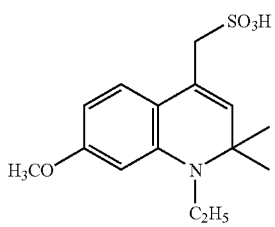 [SMILES: CCN1c2cc(OC)ccc2C(CS(=O)(=O)O)=CC1(C)C] | $C_{15}H_{21}NO_4S$ | 312 |
| 16 | 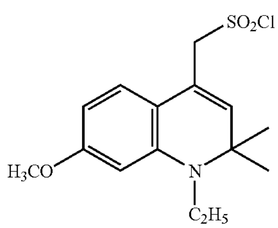 [SMILES: CCN1c2cc(OC)ccc2C(CS(=O)(=O)Cl)=CC1(C)C] | $C_{15}H_{22}ClNO_3S$ | 330 |
| 17 | 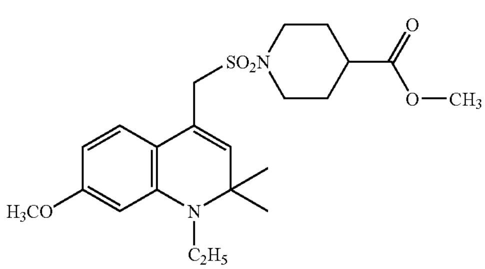 | $C_{22}H_{32}N_2O_5S$ | 437 |
| 18 | 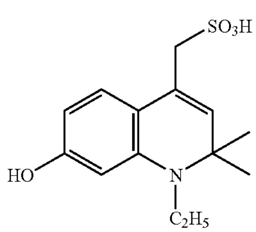 [SMILES: CCN1c2cc(O)ccc2C(CS(=O)(=O)O)=CC1(C)C] | $C_{14}H_{19}NO_4S$ | 298 |

TABLE 1-continued

Quinolylsulfonic acids and derivatives thereof

| Example | Structure | Empirical formula | Mass MH+ |
|---------|-----------|-------------------|----------|
| 19 | 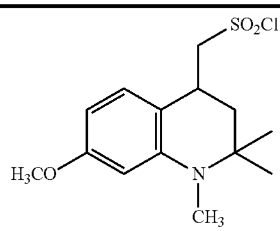 | $C_{14}H_{20}ClNO_3S$ | 318 |
| 20 | 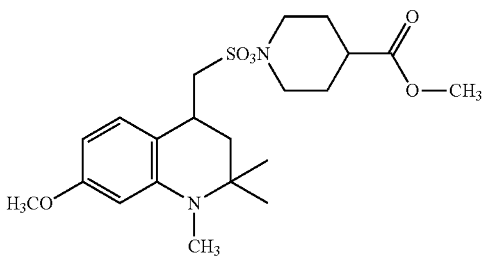 | $C_{21}H_{32}N_2O_5S$ | 425 |
| 21 | 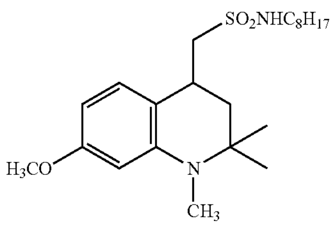 | $C_{22}H_{38}N_2O_3S$ | 411 |
| 22 | 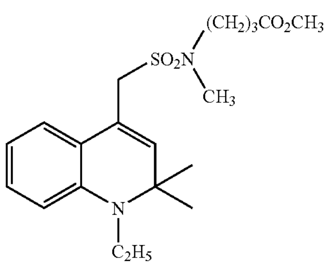 | $C_{20}H_{30}N_2O_4S$ | 395 |
| 23 | 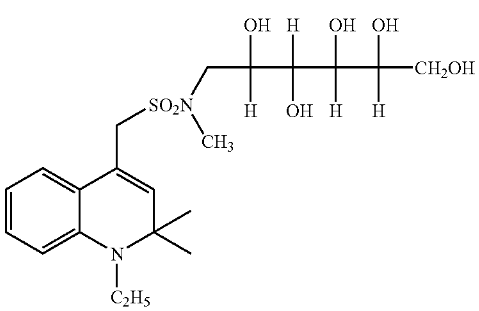 | $C_{21}H_{34}N_2O_4S$ | 459 |
| 24 | 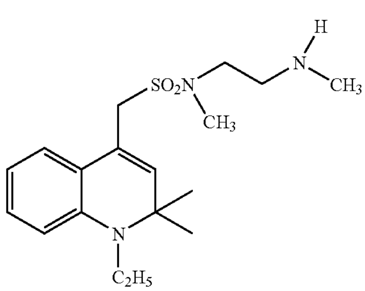 | $C_{18}H_{29}N_3O_2S$ | 352 |

TABLE 1-continued

Quinolylsulfonic acids and derivatives thereof

| Example | Structure | Empirical formula | Mass MH+ |
|---------|-----------|-------------------|----------|
| 25 | 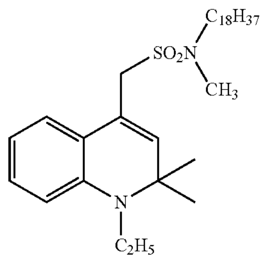 | $C_{33}H_{58}N_2O_2S$ | 547 |
| 26 | 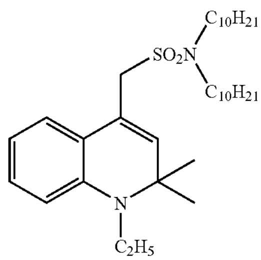 | $C_{34}H_{60}N_2O_2S$ | 561 |
| 27 | 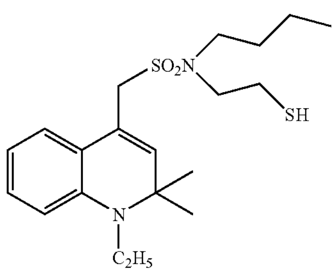 | $C_{20}H_{32}N_2O_2S_2$ | 397 |
| 28 | 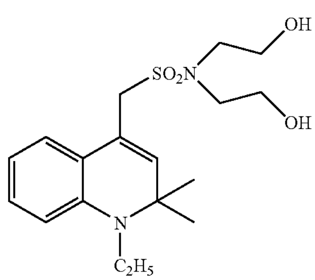 | $C_{18}H_{28}N_2O_4S$ | 369 |
| 29 | 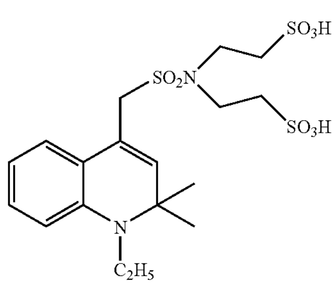 | $C_{18}H_{28}N_2O_8S_3$ | 497 |

TABLE 1-continued
Quinolylsulfonic acids and derivatives thereof
| Example | Structure | Empirical formula | Mass MH+ |
|---|---|---|---|
| 30 | 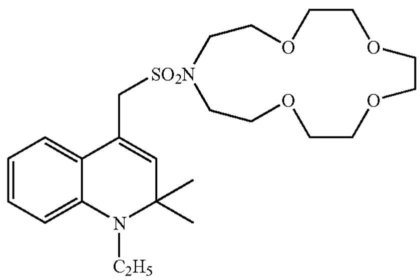 | $C_{24}H_{38}N_2O_6S$ | 483 |
| 31 | 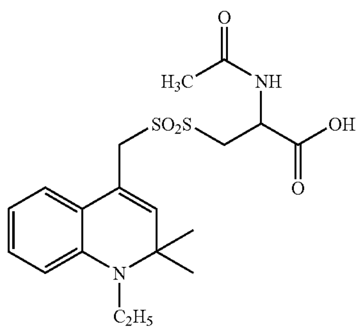 | $C_{19}H_{26}N_2O_5S_2$ | 427 |
| 32 | 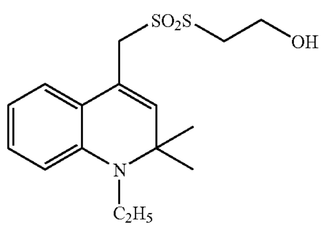 | $C_{16}H_{23}NO_2S_2$ | 341 |
| 33 | 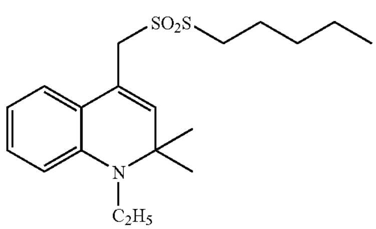 | $C_{19}H_{29}NO_2S_2$ | 367 |
TABLE 2a
Coumarin dyes with a sulfonic acid group
spectral data in ethanol:
$\lambda_a$ absorption maximum
$\lambda_f$ fluorescence maximum
| Name | Structure | $\lambda_a$/nm | $\lambda_f$/nm |
|---|---|---|---|
| 34 AZ 59 | 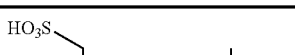 | 394 | 468 |
| 35 AZ 100 |  | 383 | 455 |

TABLE 2a-continued

Coumarin dyes with a sulfonic acid group
spectral data in ethanol:
$\lambda_a$ absorption maximum
$\lambda_f$ fluorescence maximum

| Name | Structure | $\lambda_a$/nm | $\lambda_f$/nm |
|---|---|---|---|
| 36 AZ 101 | 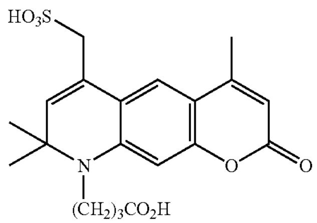 | 394 | 469 |

TABLE 2b

Rhodamine dyes with a sulfonic acid group
spectral data in ethanol:
$\lambda_a$ absorption maximum
$\lambda_f$ fluorescence maximum

| Name | Structure (anion A⁻) | $\lambda_a$/nm | $\lambda_f$/nm |
|---|---|---|---|
| 37 JA 317 | | 592 | 612 |
| 38 JA 325 | | 621 | 642 |
| 39 AZ 58 | | 562 | 587 |
| 40 JA 407 | | 623 | 645 |
| 41 JA 407-E | | 623 | 644 |

Et = $C_2H_5$

TABLE 2c

Oxazine dyes with a sulfonic acid group
spectral data in ethanol:
$\lambda_a$ absorption maximum
$\lambda_f$ fluorescence maximum

| Name | Structure (anion A⁻) | $\lambda_a$/nm | $\lambda_f$/nm |
|---|---|---|---|
| 42 JA 378 | | 655 | 680 |
| 43 JA 379 | | 675 | 699 |

TABLE 2c-continued

Oxazine dyes with a sulfonic acid group
spectral data in ethanol:
$\lambda_a$ absorption maximum
$\lambda_f$ fluorescence maximum

| Name | Structure (anion A⁻) | $\lambda_a$/nm | $\lambda_f$/nm |
|---|---|---|---|
| 44 JA 322 | | 674 | 699 |
| 45 JA 324-S | | 673 | 698 |
| 46 JA 326 | | 655 | 679 |
| 47 JA 329 | | 654 | 678 |
| 48 JA 410 | | 694 | 717 |
| 49 JA 331 | | 674 | 695 |
| 50 JA 366 | | 654 | 678 |
| 51 JA 403 | | 653 | 676 |
| 52 JA 404 | | 678 | 699 |
| 53 JA 408 | | 694 | 715 |

TABLE 2d

Carbopyronine dyes with a sulfonic acid group
spectral data in ethanol:
$\lambda_a$ absorption maximum
$\lambda_f$ fluorescence maximum

| Name | Dye (anion A⁻) | $\lambda_a$/nm | $\lambda_f$/nm |
|---|---|---|---|
| 54 JA 323 | | 637 | 664 |
| 55 AZ 30 | | 648 | 675 |
| 56 AZ 31 | | 648 | 674 |

TABLE 2d-continued

Carbopyronine dyes with a sulfonic acid group
spectral data in ethanol:
$\lambda_a$ absorption maximum
$\lambda_f$ fluorescence maximum

| Name | Dye (anion A⁻) | $\lambda_a$/nm | $\lambda_f$/nm |
|---|---|---|---|
| 57 AZ 35 | | 649 | 674 |
| 58 AZ 8-SO₃H | | 641 | 666 |
| 59 AZ 9-SO₃H | | 647 | 675 |
| 60 AZ 10-SO₃H | | 637 | 664 |
| 61 AZ 11-SO₃H | | 664 | 688 |
| 62 AZ 12-SO₃H | | 647 | 674 |

TABLE 2e

Amidopyrylium dyes with a sulfonic acid group
spectral data in ethanol:
$\lambda_a$ absorption maximum
$\lambda_f$ fluorescence maximum

| Name | Structure (anion A⁻) | $\lambda_a$/nm | $\lambda_f$/nm |
|---|---|---|---|
| 63 NK 32 | | 635 | 695 |
| 64 NK 34 | | 610 | 668 |

TABLE 3a

Sulfonic acid derivatives of coumarin dyes according to the invention
spectral data in ethanol:
$\lambda_a$ absorption maximum
$\lambda_f$ fluorescence maximum

| Name | Structure | $\lambda_a$/nm | $\lambda_f$/nm |
|---|---|---|---|
| 65 AZ 96 | 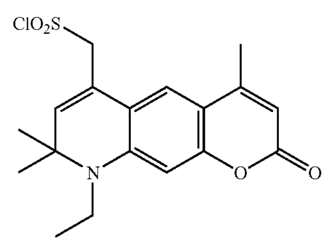 [SMILES: CCN1c2cc3oc(=O)cc(C)c3cc2C(CS(=O)(=O)Cl)=CC1(C)C] | 394 | 468 |
| 66 AZ 97 | 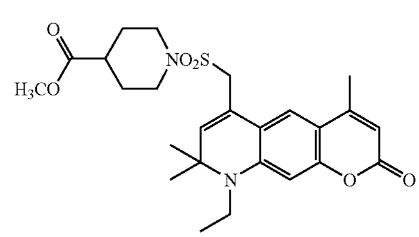 | 393 | 468 |

TABLE 3a-continued

Sulfonic acid derivatives of coumarin dyes according to the invention
spectral data in ethanol:
$\lambda_a$ absorption maximum
$\lambda_f$ fluorescence maximum

| Name | Structure | $\lambda_a$/nm | $\lambda_f$/nm |
|---|---|---|---|
| 67 AZ 98 | 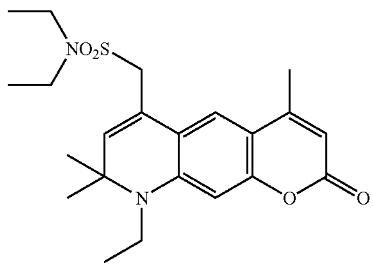 | 394 | 467 |
| 68 AZ 99 | 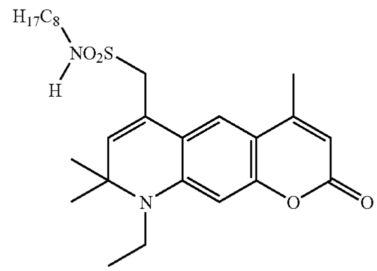 | 393 | 469 |

TABLE 3b

Sulfonic acid derivatives of rhodamine dyes according to the invention
spectral data in ethanol:
$\lambda_a$ absorption maximum
$\lambda_f$ fluorescence maximum

| Name | Structure (anion A⁻) | $\lambda_a$/nm | $\lambda_f$/nm |
|---|---|---|---|
| 69 AZ 49 | | 542 | 567 |
| 70 AZ 50 | | 561 | 587 |
| 71 AZ 84 | | 624 | 644 |

Et = C₂H₅

TABLE 3b-continued

Sulfonic acid derivatives of rhodamine dyes according to the invention
spectral data in ethanol:
$\lambda_a$ absorption maximum
$\lambda_f$ fluorescence maximum

| Name | Structure (anion A⁻) | $\lambda_a$/nm | $\lambda_f$/nm |
|---|---|---|---|
| 72 AZ 85 | | 624 | 644 |
| 73 AZ 86 | | 624 | 645 |
| 74 AZ 88 | | 623 | 644 |
| 75 AZ 89 | | 624 | 644 |

TABLE 3b-continued

Sulfonic acid derivatives of rhodamine dyes according to the invention
spectral data in ethanol:
$\lambda_a$ absorption maximum
$\lambda_f$ fluorescence maximum

| Name | Structure (anion A⁻) | $\lambda_a$/nm | $\lambda_f$/nm |
|---|---|---|---|
| 76 AZ 90 | | 624 | 645 |
| 77 AZ 87 | | 624 | 644 |
| 78 AZ 93 | | 624 | 644 |
| 79 AZ 94 | | 624 | 646 |

TABLE 3b-continued
Sulfonic acid derivatives of rhodamine dyes according to the invention
spectral data in ethanol:
$\lambda_a$ absorption maximum
$\lambda_f$ fluorescence maximum
| Name | Structure (anion A⁻) | $\lambda_a$/nm | $\lambda_f$/nm |
|---|---|---|---|
| 80 AZ 95 | 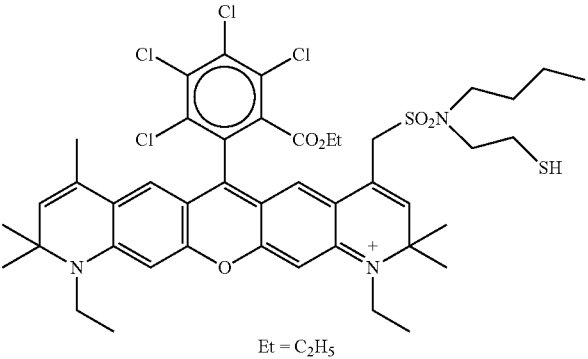 | 624 | 644 |
| 81 AZ 91 | 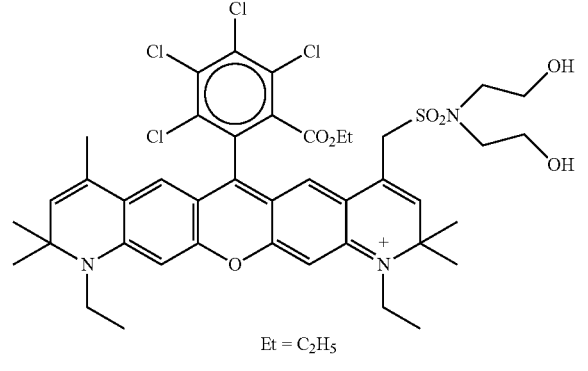 | 624 | 646 |
| 82 AZ 92 | 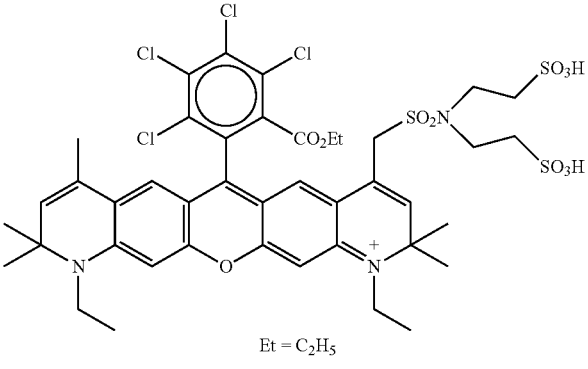 | 624 | 644 |

TABLE 3c

Sulfonic acid derivatives of oxazine dyes according to the invention
spectral data in ethanol:
$\lambda_a$ absorption maximum
$\lambda_f$ fluorescence maximum

| Name | Structure (anion A⁻) | $\lambda_a$/nm | $\lambda_f$/nm |
|---|---|---|---|
| 83 AZ 46 | (structure with $SO_2Cl$) | 654 | 680 |
| 84 JA 403 ME | (structure with $SO_2OCH_3$) | 654 | 679 |
| 85 AZ 54 | (structure with $SO_2N(H)-C_8H_{17}$) | 653 | 677 |
| 86 AZ 55 | (structure with $SO_2N(C_2H_5)_2$) | 654 | 679 |
| 87 AZ 56 | (structure with $SO_2N$-piperidine-$COOCH_3$) | 653 | 678 |
| 88 AZ 52 | (structure with $SO_2N$-piperidine-$COOC_2H_5$) | 678 | 699 |

TABLE 3c-continued

Sulfonic acid derivatives of oxazine dyes according to the invention
spectral data in ethanol:
$\lambda_a$ absorption maximum
$\lambda_f$ fluorescence maximum

| Name | Structure (anion A⁻) | $\lambda_a$/nm | $\lambda_f$/nm |
|---|---|---|---|
| 89 AZ 57 | | 653 | 677 |
| 90 AZ 102 | | 654 | 678 |
| 91 AZ 73 | | 678 | 717 |
| 92 AZ 74 | | 678 | 715 |
| 93 AZ 75 | | 679 | 715 |

TABLE 3c-continued

Sulfonic acid derivatives of oxazine dyes according to the invention
spectral data in ethanol:
$\lambda_a$ absorption maximum
$\lambda_f$ fluorescence maximum

| Name | Structure (anion A⁻) | $\lambda_a$/nm | $\lambda_f$/nm |
|---|---|---|---|
| 94 AZ 76 | | 678 | 715 |
| 95 AZ 77 | | 678 | 716 |
| 96 AZ 78 | | 677 | 714 |
| 97 AZ 79 | | 678 | 716 |
| 98 AZ 80 | | 678 | 715 |

TABLE 3c-continued

Sulfonic acid derivatives of oxazine dyes according to the invention
spectral data in ethanol:
$\lambda_a$ absorption maximum
$\lambda_f$ fluorescence maximum

| Name | Structure (anion A⁻) | $\lambda_a$/nm | $\lambda_f$/nm |
|---|---|---|---|
| 99 AZ 81 | | 679 | 715 |

TABLE 3d

Sulfonic acid derivatives of carbopyronine dyes according to the invention
spectral data in ethanol:
$\lambda_a$ absorption maximum
$\lambda_f$ fluorescence maximum

| Name | Structure (anion A⁻) | $\lambda_a$/nm | $\lambda_f$/nm |
|---|---|---|---|
| 100 AZ 48 | | 634 | 658 |
| 101 AZ 64 | | 635 | 661 |
| 102 AZ 65 | | 634 | 661 |

TABLE 3d-continued

Sulfonic acid derivatives of carbopyronine dyes according to the invention
spectral data in ethanol:
$\lambda_a$ absorption maximum
$\lambda_f$ fluorescence maximum

| Name | Structure (anion A⁻) | $\lambda_a$/nm | $\lambda_f$/nm |
|---|---|---|---|
| 103 AZ 66 | | 635 | 663 |
| 104 AZ 67 | | 635 | 663 |
| 105 AZ 68 | | 634 | 662 |
| 106 AZ 69 | | 634 | 661 |
| 107 AZ 70 | | 634 | 662 |

TABLE 3d-continued

Sulfonic acid derivatives of carbopyronine dyes according to the invention spectral data in ethanol:

$\lambda_a$ absorption maximum $\lambda_f$ fluorescence maximum

| Name | Structure (anion A⁻) | $\lambda_a$/nm | $\lambda_f$/nm |
| --- | --- | --- | --- |
| 108 AZ 71 | | 634 | 662 |
| 109 AZ 72 | | 635 | 661 |
| 110 AZ 82 | | 634 | 661 |
| 111 AZ 83 | | 635 | 663 |

TABLE 3e

Sulfonic acid derivatives of trifluoromethyl-substituted xanthene dyes according to the invention
spectral data in ethanol:
$\lambda_a$ absorption maximum
$\lambda_f$ fluorescence maximum

| Name | Structure (anion A⁻) | $\lambda_a$/nm | $\lambda_f$/nm |
|---|---|---|---|
| 112 AZ 51 | | 665 | 694 |
| 113 AZ 63 | | 664 | 694 |
| 114 AZ 60 | | 651 | 680 |
| 115 AZ 62 | | 652 | 680 |
| 116 AZ 61 | | 652 | 679 |

EXAMPLES

The invention is elucidated in more detail by the following examples. Examples are given for the production of sulfonated quinoline precursors and their derivatization as well as examples for the synthesis and modification of dyes from appropriately-sulfonated quinolines. The dihydroquinolines and tetrahydroquinolines and primary or secondary amines used as starting compounds for the compounds described under 1. are either commercially available or can be prepared by syntheses known from the literature or methods known to a person skilled in the art. This also applies to the starting dyes for the dye derivatives described under 2.

1. Precursors: Production of Compounds According to the Invention

Compound 8

In order to prepare (1-ethyl-2,2-dimethyl-1,2-dihydroquinol-4-yl)-methanesulfonic acid (8), 6.0 g (21 mmol) 1-ethyl-2,2,4-dimethyl-1,2-dihydroquinoline is dissolved while cooling on ice in a mixture of 10 ml concentrated sulfuric acid and oleum in a ratio of 5:1. It is stirred for 20 hours at room temperature. The reaction mixture is poured onto ice and made alkaline (pH 12) with 20% sodium hydroxide solution while cooling with ice/methanol. In order to remove the non-reacted educt, it is extracted with chloroform and the aqueous phase is evaporated to dryness on a rotary evaporator. The crystalline residue is suspended in ethanol, the sodium sulfate is removed by suction filtration and the organic phase is evaporated to dryness on a rotary evaporator. The resinous residue crystallizes on addition of acetone. It is again suction filtered, washed with acetone and dried over phosphorus pentoxide under a vacuum. The crude product that is obtained can be used in the next step without further purification steps.

Yield 82%.

ESI mass spectrum: m/z=282 (MH$^+$)

NMR (DMSO-d$_6$): C$\underline{H}_3$CH$_2$—, 0.97 ppm, T, 3; —C$\underline{H}_2$—N, 3.39 ppm, Q, 2; 2×C$\underline{H}_3$—, 1.31 ppm, S, 6; =C$\underline{H}$, 5.74 ppm, S, 1; —C$\underline{H}_2$SO$_3$H, 4.27 ppm, S, 2; $\underline{H}$ aromatic, 7.15-7.58 ppm, M, 4.

Compound 9

In order to prepare (1-ethyl-2,2-dimethyl-1,2-dihydroquinol-4-yl)-methanesulfonic acid chloride (9), 2.5 g (8.8 mmol) (1-ethyl-2,2-dimethyl-1,2-dihydroquinol-4-yl)-methanesulfonic acid (8) is suspended in 70 ml dry benzene and 4.6 g (22.2 mmol) phosphorus pentachloride is added in portions at room temperature. The reaction mixture firstly becomes yellow coloured and later yellow-orange. The white precipitate is removed by filtration after 1.5 hours and washed with cold dry benzene. It is dried in a vacuum over phosphorus pentoxide. The acid chloride that is obtained is used immediately in the next step without further purification.

Yield 75%.

ESI mass spectrum: m/z=300 (MH$^+$)

Compound 10

In order to prepare (1-ethyl-2,2-dimethyl-1,2-dihydroquinol-4-yl-methanesulfonyl)-piperidine-4-carboxylic acid methyl ester (10), 2 g (6.6 mmol) (1-ethyl-2,2-dimethyl-1,2-dihydroquinol-4-yl)-methanesulfonic acid chloride (9) is dissolved in 40 ml dry acetonitrile and cooled in an ice bath. 1.13 g (7.9 mmol) 4-piperidine-carboxylic acid methyl ester followed by 0.85 g (6.6 mmol) diisopropylethylamine are added dropwise. The reaction mixture is stirred for 30 minutes at room temperature. Water is added and the mixture is extracted with chloroform, washed with 10% cold soda solution and dried over anhydrous sodium sulfate. The solvent is removed by distillation on a rotary evaporator and the residue is purified by column chromatography on silica gel with a gradient running from chloroform to ethanol.

Yield 82%.

ESI mass spectrum: m/z=407 (MH$^+$)

Compound 13

In order to prepare 1-(1-ethyl-6-formyl-2,2-dimethyl-1,2-dihydroquinol-4-yl-methane-sulfonyl)-piperidine-4-carboxylic acid methyl ester (13), 3 ml dry dimethylformamide is cooled in an ice/methanol bath to −10° C. and 0.45 ml (4.9 mmol) phosphoryl trichloride is added dropwise. The reaction mixture is stirred for 20 minutes at −5° C. (1-Ethyl-2,2-dimethyl-1,2-dihydroquinol-4-yl-methane-sulfonyl)-piperidine-4-carboxylic acid methyl ester (10) is dissolved in 1.5 ml dry dimethylformamide and added dropwise to the reaction mixture at −5° C. After the addition is completed, the mixture is heated for 50 minutes to 80° C. The reaction solution is poured onto iced water and chloroform is added. It is adjusted to pH 12 with 20% sodium hydroxide solution and extracted several times with chloroform. The organic phase is washed with 10% soda solution and dried over anhydrous sodium sulfate. The crude product that is obtained is evaporated to dryness under a vacuum in a rotary evaporator and purified by column chromatography on silica gel by means of a gradient running from chloroform to ethanol.

Yield 88%.

ESI mass spectrum: m/z=435 (MH$^+$)

NMR (CDCl$_3$): C$\underline{H}_3$CH$_2$—, 1.22 ppm, T, 3; —C$\underline{H}_2$—N, 3.41 ppm, Q, 2; 2×C$\underline{H}_3$—, 1.42 ppm, S, 6; =C$\underline{H}$, 5.63 ppm, S, 1; —C$\underline{H}_2$SO$_2$N, 4.00 ppm, S, 2; $\underline{H}$-5 aromatic, 7.59 ppm, S, 1; $\underline{H}$-7 aromatic, 7.57 ppm, D, 1; $\underline{H}$-8 aromatic, 6.55 ppm, D, 1; $\underline{H}$—C=O, 9.68 ppm, S, 1; —O—C$\underline{H}_3$, 3.63 ppm, S, 1; C$\underline{H}$ (piperidine)-C=O, 2.31 ppm, M, 1; N—C$\underline{HH}$' (piperidine), 2.83 ppm and 3.52 ppm; M, 2.2; HC—C$\underline{HH}$' (piperidine), 1.67 ppm and 1.83 ppm; M, 2.2.

Compound 14

In order to prepare 1-(1-ethyl-6-hydroxymethyl-2,2-dimethyl-1,2-dihydroquinol-4-yl-methane sulfonyl)-piperidine-4-carboxylic acid methyl ester (14), 1 g (2.3 mmol) 1-(1-ethyl-6-formyl-2,2-dimethyl-1,2-dihydroquinol-4-yl-methanesulfonyl)-piperidine-4-carboxylic acid methyl ester (13) is dissolved in 10 ml ethanol and 0.05 g sodium borohydride is added while cooling on ice during which a considerable gas evolution with foaming is observed. It is stirred for 50 minutes at room temperature. In order to decompose the excess of reducing agent, 1 N hydrochloric acid is added dropwise until no more foaming is observed (pH 7). It is poured onto 50 ml water and extracted 3 times with 20 ml chloroform. The combined organic phases are dried over anhydrous sodium sulfate and the solvent is removed by distillation until dryness in a rotary evaporator. The residue that is obtained is purified by column chromatography on silica gel using a gradient running from chloroform to ethanol.

Yield 88%.

ESI mass spectrum: m/z=435 (MH$^+$)

NMR (CDCl$_3$): C$\underline{H}_3$CH$_2$—, 1.10 ppm, T, 3; —C$\underline{H}_2$—N, 3.25 ppm, Q, 2; 2×C$\underline{H}_3$—, 1.27 ppm, S, 6; =C$\underline{H}$, 5.53 ppm, S, 1; —C$\underline{H}_2$SO$_2$N, 3.96 ppm, S, 2; $\underline{H}$-5 aromatic, 7.10 ppm, S, 1; $\underline{H}$-7 aromatic, 7.05 ppm D, 1; $\underline{H}$-8 aromatic, 6.46 ppm, D, 1; $\underline{H}_2$C—OH, 4.47 ppm, S, 1; —O—C$\underline{H}_3$, 3.57 ppm, S, 1; C$\underline{H}$ (piperidine)-C=O, 2.29 ppm, M, 1; N—C$\underline{HH}$' (piperidine), 2.82 ppm and 3.53 ppm; M, 2.2; HC—C$\underline{HH}$' (piperidine), 1.68 ppm and 1.73 ppm; M, 2,2; —CH$_2$—O$\underline{H}$, nn.

Compound 3

In order to prepare (1-methyl-7-methoxy-2,2-dimethyl-1,2,3,4-tetrahydroquinol-4-yl)-methanesulfonic acid (3), 5.0 g (1-methyl-7-methoxy-2,2-dimethyl-1,2-dihydro-quinol-4-yl)-methanesulfonic acid is dissolved in 100 ml methanol and 0.5 g 10% palladium on activated carbon is added. The reaction mixture is hydrogenated for 18 hours at 70 bar and room temperature in an autoclave. It is filtered and evaporated to dryness on a rotary evaporator. The solid that is obtained can be used in the next step without further purification.

Yield 90%.

ESI mass spectrum: m/z=270 (MH$^+$)

Compound 11

N,N-diethyl-(1-ethyl-2,2-dimethyl-1,2-dihydroquinol-4-yl)-methanesulfon-amide (11) is prepared similarly to compound (10) using compound (9) with diethylamine. The product is isolated by column chromatography on silica gel with a gradient running from chloroform to ethanol.

Yield 79%.

ESI mass spectrum: m/z=337 (MH$^+$)

Compound 12

(1-Ethyl-2,2-dimethyl-1,2-dihydroquinol-4-yl)-N-octyl-methanesulfonamide (12) is prepared similarly to compound (10) using compound (9) with n-octylamine. The product is isolated by column chromatography on silica gel with a gradient running from chloroform to ethanol.

Yield 81%.

ESI mass spectrum: m/z=393 (MH$^+$)

Compound 15

In order to prepare (1-ethyl-7-methoxy-2,2-dimethyl-1,2-dihydroquinol-4-yl)-methanesulfonic acid (15), 20 g (8.6 mmol) 1-ethyl-7-methoxy-2,2,4-dimethyl-1,2-dihydroquinoline is dissolved in a mixture of 10 ml concentrated sulfuric acid and oleum in a ratio of 5:1 while cooling on ice. It is stirred for 20 hours at room temperature. The reaction mixture is poured onto ice and made alkaline (pH 12) with 20% sodium hydroxide solution while cooling with ice/methanol. In order to remove the non-reacted educt, it is extracted with chloroform and the aqueous phase is evaporated to dryness in a rotary evaporator. The crystalline residue is purified by column chromatography on silica gel with a gradient running from chloroform to ethanol.

Yield 86%.

ESI mass spectrum: m/z=312 (MH$^+$)

NMR (DMSO-d$_6$): C$\underline{H}_3$CH$_2$—, 1.09 ppm, T, 3; —C$\underline{H}_2$—N, 3.25 ppm, Q, 2; 2×C$\underline{H}_3$—, 1.24 ppm, S, 6; =C$\underline{H}$, 5.28 ppm, S, 1; —C$\underline{H}_2$SO$_3$H, 3.43 ppm, S, 2; $\underline{H}$-5 aromatic, 6.04 ppm, D, 1; $\underline{H}$-6 aromatic, 7.17 ppm, D, 1; $\underline{H}$-8 aromatic, 5.93 ppm, S, 1; CH$_3$O—, 3.68 ppm, S, 3.

Compound 16

(1-Ethyl-7-methoxy-2,2-dimethyl-1,2-dihydroquinol-4-yl)-methanesulfonic acid chloride (16) is prepared similarly to compound (9) from compound (15) and phosphorus pentachloride in dry benzene. The acid chloride that is obtained is immediately used for further reaction.

Yield 73%.

ESI mass spectrum: m/z=330 (MH$^+$)

Compound 17

(1-Ethyl-7-methoxy-2,2-dimethyl-1,2-dihydroquinol-4-yl-methanesulfonyl)-piperidine-4-carboxylic acid methyl ester (17) is prepared similarly to compound (10) from compound (16) in dry acetonitrile at room temperature.

Yield 69%.

ESI mass spectrum: m/z=437 (MH$^+$)

NMR (CDCl$_3$): C$\underline{H}_3$CH$_2$—, 1.15 ppm, T, 3; —C$\underline{H}_2$—N, 3.27 ppm, Q, 2; 2×C$\underline{H}_3$—, 1.31 ppm, S, 6; =C$\underline{H}$, 5.41 ppm, S, 1; —C$\underline{H}_2$SO$_2$N, 3.97 ppm, S, 2; $\underline{H}$-5 aromatic, 6.17 ppm, D, 1; $\underline{H}$-6 aromatic, 7.07 ppm, D, 1; $\underline{H}$-8 aromatic, 6.09 ppm, S, 1; —O—C$\underline{H}_3$, 3.77 ppm, S, 1; C$\underline{H}$(piperidine)-C=O, 2.31 ppm, M, 1; N—C$\underline{HH}$' (piperidine), 2.82 ppm and 3.63 ppm; M, 2.2; HC—C$\underline{HH}$' (piperidine), 1.63 ppm and 1.80 ppm; M, 2.2; O=C—OC$\underline{H}_3$, 3.63, S, 3.

Compound 18

In order to prepare (1-ethyl-7-hydroxy-2,2-dimethyl-1,2-dihydroquinol-4-yl)-methanesulfonic acid (18), 5 g (16.1 mmol) (1-ethyl-7-methoxy-2,2-dimethyl-1,2-dihydroquinol-4-yl)-methanesulfonic acid (16) is suspended in 10 ml 48% hydrobromic acid and refluxed for 2 hours. It is poured onto ice, chloroform is added and it is neutralized with 20% sodium hydroxide solution. The organic phase is separated and the aqueous phase is evaporated to dryness in a vacuum on a rotary evaporator. The residue is suspended in hot ethanol, filtered and the filtrate is again rotary evaporated to dryness. The product obtained in this manner is used in the next step without further purification.

Yield 91%.

ESI mass spectrum: m/z=298 (MH$^+$)

Compound 19

(1-Methyl-7-methoxy-2,2-dimethyl-1,2,3,4-tetrahydroquinol-4-yl)-methane-sulfonic acid chloride (19) is prepared similarly to compound (16) using compound (3) and phosphorus pentachloride except that it is stirred for 18 hours at room temperature.

Yield 78%.

ESI mass spectrum: m/z=317 (MH$^+$)

Compound 20

(1-Methyl-7-methoxy-2,2-dimethyl-1,2,3,4-tetrahydroquinol-4-yl-methane-sulfonyl)-piperidine-4-carboxylic acid methyl ester (20) is prepared similarly to compound (10) from compound (19) and 4-piperidinecarboxylic acid methyl ester in dry acetonitrile. It is isolated by column chromatography on silica gel using a gradient running from chloroform to ethanol.

Yield 69%.

ESI mass spectrum: m/z=425 (MH$^+$)

Compound 21

(1-Methyl-7-methoxy-2,2-dimethyl-1,2,3,4-tetrahydroquinol-4-yl)-N-octyl-methane-sulfonamide (21) is prepared similarly to compound (10) from compound (19) and n-octylamine in dry acetonitrile. It is isolated by column chromatography on silica gel using a gradient running from chloroform to ethanol.

Yield 69%.

ESI mass spectrum: m/z=411 (MH$^+$)

2. Dyes: Production of Compounds According to the Invention

Compound 55 (AZ 30)

1.2 g (4.93 mmol) 4-(6-hydroxymethyl-2,2,4-trimethyl-2H-quinol-1-yl)-butyric acid ethyl ester and 0.72 g (4.93 mmol) 1-ethyl-6-isopropenyl-indoline are dissolved in 20 ml dry dichloromethane and cooled to −5° C. 7 ml of a 1 molar solution of boron trichloride in dichloromethane is added dropwise. The reaction mixture is stirred for 2 hours at room temperature, the solvent is removed in a rotary evaporator and the residue is dissolved in concentrated sulfuric acid. The reaction mixture is stirred for 4 hours at room temperature. The reaction mixture is added dropwise to ice-cold ethanol, 0.8 g tetrabutylammonium metaperiodate is added and the mixture is briefly heated to boiling point. It is allowed to cool, water is added and the dye is taken up in chloroform. It is dried over anhydrous sodium sulfate and the dye solution is evaporated to dryness in a rotary evaporator. The crude dye product that is obtained is purified by column chromatography on silica gel with a gradient running from chloroform to ethanol.

Yield 45%.

ESI mass spectrum: m/z=565 (M$^+$)

absorption maximum: $\lambda_a$=648 nm (in ethanol)

Compound 83 (AZ 46)

100 mg (0.21 mmol) JA 403 is dissolved in 8 ml dry acetonitrile and cooled in a cold water bath. 4 drops of dry dimethylformamide followed by 6 drops of freshly distilled thionyl chloride are added. It is stirred for 45 minutes. The reaction is quantitative. The reaction mixture is cooled in an ice bath. The dye solution is added dropwise to a 20% sodium perchlorate solution cooled with ice/methanol. The dye which precipitates as fine crystals is suction filtered, washed with a small amount of cold water and dried over phosphorus pentoxide in an oil pump vacuum. The dye can be used for further reactions without additional purification.

Yield 81%.
ESI mass spectrum: m/z=502 (M$^+$)
absorption maximum: $\lambda_a$=650 nm (acetonitrile)

Compound 90 (AZ 102)

10 mg (0.017 mmol) AZ 46 is dissolved in 5 ml dry acetonitrile and 5 ml of a 10 mmolar solution of benzylamine in dry acetonitrile is added. The reaction mixture is stirred for 20 minutes at room temperature. The reaction solution is evaporated to dryness on a rotary evaporator and purified by column chromatography on silica gel with a gradient running from chloroform to ethanol.

Yield 88%.
ESI mass spectrum: m/z=573 (M$^+$)
absorption maximum: $\lambda_a$=653 nm (in ethanol)

Compound 87 (AZ 56)

The synthesis is carried out similarly to the preparation of AZ 102 using a 10 mmolar solution of 4-piperidinecarboxylic acid methyl ester. It is isolated by column chromatography on silica gel using a gradient running from chloroform to ethanol.

Yield 91%.
ESI mass spectrum: m/z=609 (M$^+$)
absorption maximum: $\lambda_a$=652 nm (in ethanol)

Compound 89 (AZ 57)

10 mg (0.014 mmol) AZ 56 is dissolved in 20 ml acetonitrile/water 1:1 and 0.5 ml 2 N hydrochloric acid is added. The reaction mixture is refluxed for 7 hours. The dye solution is evaporated under a vacuum and purified by column chromatography on silica gel using a gradient running from chloroform to ethanol.

Yield 62%.
ESI mass spectrum: m/z=595 (M$^+$)
absorption maximum: $\lambda_a$=652 nm (in ethanol)

Compound 34 (AZ 59)

500 mg (1.7 mmol) (1-ethyl-7-hydroxy-2,2-dimethyl-1,2-dihydroquinol-4-yl)-methanesulfonic acid (18), 440 mg (3.4 mmol) ethyl acetoacetate and 460 mg dry zinc chloride are suspended in 40 ml absolute ethanol and refluxed for 24 hours. The reaction mixture is filtered, evaporated to dryness in a rotary evaporator and the residue is purified by column chromatography on silica gel using a gradient running from chloroform to ethanol.

Yield 60%.
ESI mass spectrum: m/z=364 (MH$^+$)
absorption maximum: $\lambda_a$=394 nm (in ethanol)

Compound 71 (AZ 84)

It is synthesized similarly to AZ 46 using JA 407-E and thionyl chloride/DMF in dry acetonitrile. The dye that is obtained is isolated as a perchlorate and dried. The dye sulfochloride can be immediately reacted further without additional purification.

Yield 81%.
ESI mass spectrum: m/z=811 (M$^+$)
absorption maximum: $\lambda_a$=623 nm (in ethanol)

Compound 72 (AZ 85)

It is prepared similarly to AZ 102 using AZ 84 and n-octylamine in dry acetonitrile. It is isolated by column chromatography on silica gel with a gradient running from chloroform to ethanol.

Yield 73%.
ESI mass spectrum: m/z=904 (M$^+$)

Compound 65 (AZ 96)

It is prepared similarly to compound (9) from AZ 59 and phosphorus pentachloride in benzene but the stirring is carried out for 6 hours at room temperature.

Yield 63%.
ESI mass spectrum: m/z=383.2 (MH$^+$)
absorption maximum: $\lambda_a$=392 nm (in ethanol)

Compound 66 (AZ 97)

It is prepared similarly to AZ 102 from AZ 96 and 4-piperidinecarboxylic acid ethyl ester. It is isolated by column chromatography on silica gel with a gradient running from chloroform to ethanol.

Yield 76%.
ESI mass spectrum: m/z=489.2 (MH$^+$)
absorption maximum: $\lambda_a$=393 nm (in ethanol)

Compound 84 (JA 403 ME)

100 mg (0.17 mmol) JA 403 and 0.5 ml dimethylsulfate are dissolved in 20 ml dry acetonitrile and refluxed for ca. 5 hours. The reaction is monitored by thin layer chromatography. After the reaction is completed, the reaction mixture is evaporated to dryness, taken up in a small amount of chloroform and the residue is purified by column chromatography on silica gel with a gradient running from chloroform to ethanol.

Yield 70%.
ESI mass spectrum: m/z=498 (M$^+$)
absorption maximum: $\lambda_a$=654 nm (in ethanol)

What is claimed is:

1. A process for the production of dyes of the general formulae II to VII containing —SO$_2$X

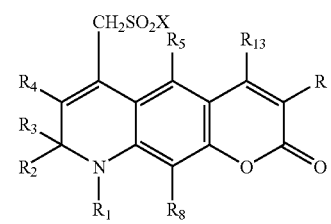

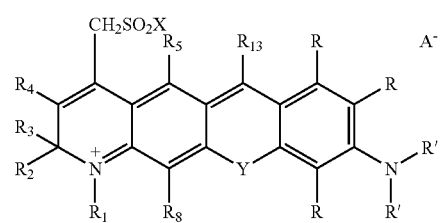

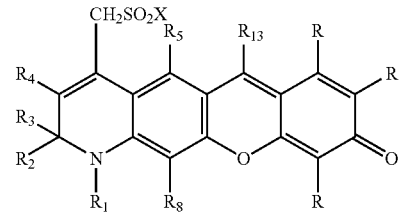

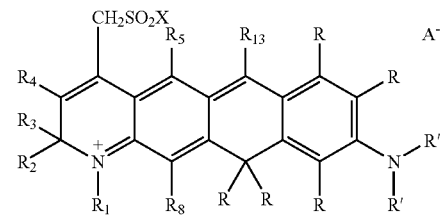

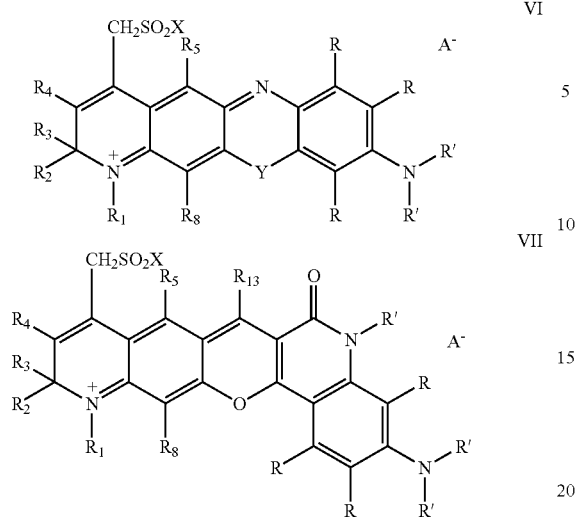

in which R' represents hydrogen or a hydrocarbon group with 1-20 C atoms where the hydrocarbon group can optionally contain one or more heteroatoms or/and one or more substituents, R on each occurrence and independently represents hydrogen, halogen, a hydroxy, amino, sulfo, carboxy or aldehyde group or a hydrocarbon group with 1-20 C atoms where the hydrocarbon group can optionally contain one or more heteroatoms or/and one or more substituents, or R and R' together form a 5-membered or 6-membered heterocyclic ring which can contain one or more multiple bonds, and in which $R_1$ represents hydrogen or a hydrocarbon group with 1-20 C atoms where the hydrocarbon group can optionally contain one or more heteroatoms or/and one or more substituents, $R_2$, $R_3$, $R_4$, $R_5$, and $R_8$ on each occurrence and independently of one another represent hydrogen, halogen, a hydroxy, amino, sulfo, carboxy or aldehyde group or a hydrocarbon group with 1-20 C atoms where the hydrocarbon group can optionally contain one or more heteroatoms or/and one or more substituents, and $R_{13}$ on each occurrence and independently represents hydrogen or a hydrocarbon group with 1-20 C atoms where the hydrocarbon group can optionally contain one or more heteroatoms or/and one or more substituents, where X represents $-S-R_{10}$ or $-NR_{11}R_{12}$ where $R_{10}$, $R_{11}$ and $R_{12}$ each independently of one another represents hydrogen or a $C_1$ to $C_{20}$ hydrocarbon which can optionally contain one or more heteroatoms or one or more substituents, and Y in formula III represents O, S or Se and Y in formula VI represents O, S or $C(R)_2$, comprising sulfonating compounds of formulae II' to VII'

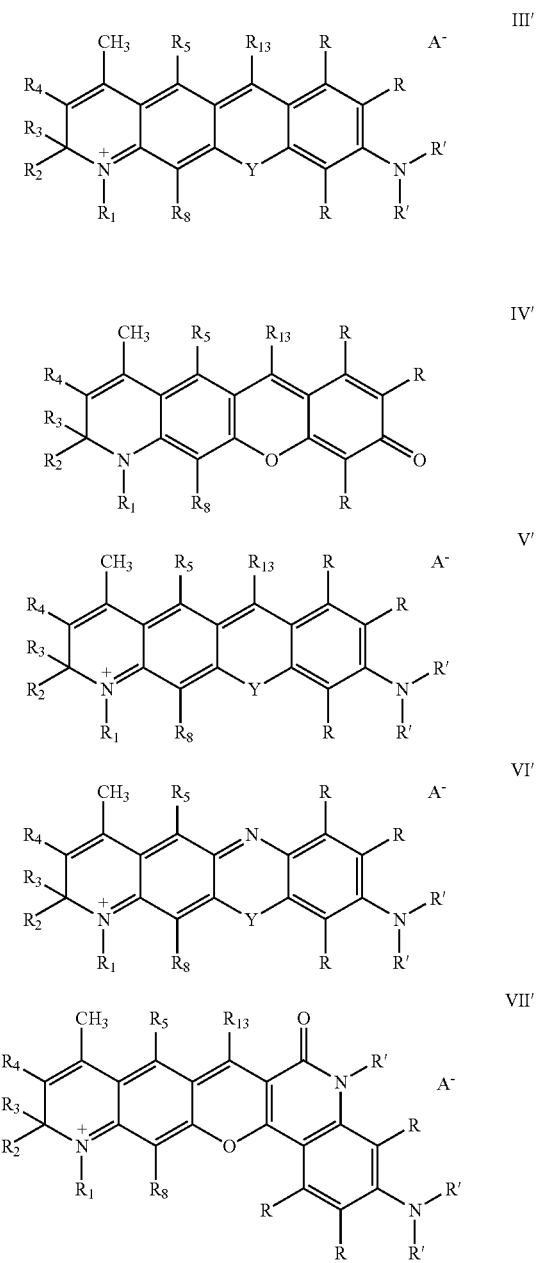

wherein y in formula V' is $C(R)_2$.

2. The polycyclic dye produced according to the process as claimed in claim 1.

3. A polycyclic dye of the general formulae II to VII

-continued

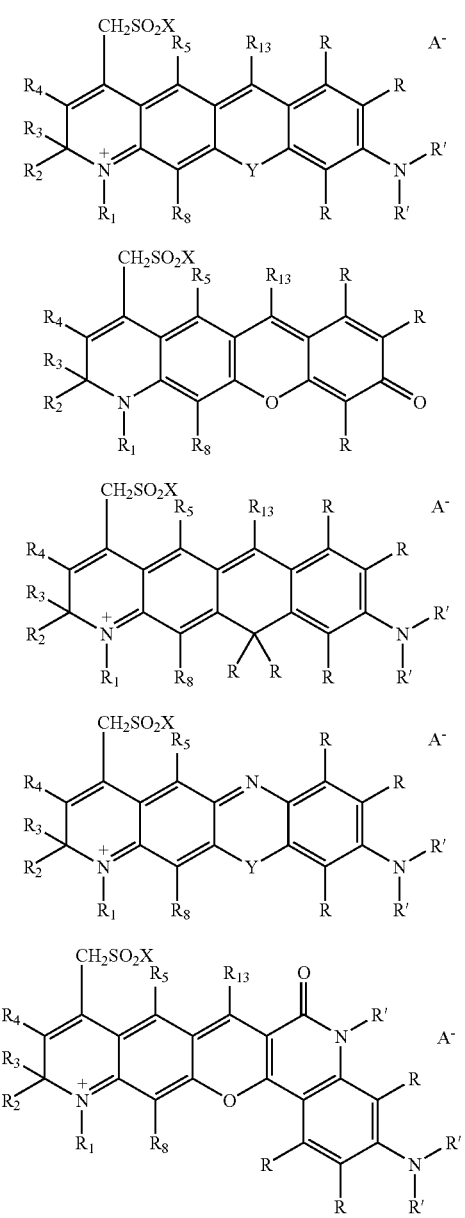

III
IV
V
VI
VII in which

R' represents hydrogen or a hydrocarbon group with 1-20 C atoms where the hydrocarbon group can optionally contain one or more heteroatoms or/and one or more substituents, R on each occurrence and independently of one another represents hydrogen, halogen, a hydroxy, amino, sulfo, carboxy or aldehyde group or a hydrocarbon group with 1-20 C atoms where the hydrocarbon group can optionally contain one or more heteroatoms or/and one or more substituents, or R' and R together form a 5-membered or 6-membered heterocyclic ring which can contain one or more multiple bonds, in which $R_1$ represents hydrogen or a hydrocarbon group with 1-20 C atoms where the hydrocarbon group can optionally contain one or more heteroatoms or/and one or more substituents, $R_2$, $R_3$, $R_4$, $R_5$, and $R_8$ on each occurrence and independently of one another represent hydrogen, halogen, a hydroxy, amino, sulfo, carboxy or aldehyde group or a hydrocarbon group with 1-20 C atoms where the hydrocarbon group can optionally contain one or more heteroatoms or/and one or more substituents, and $R_{13}$ on each occurrence and independently of one another represents hydrogen or a hydrocarbon group with 1-20 C atoms where the hydrocarbon group can optionally contain one or more heteroatoms or/and one or more substituents, X is —S—$R_{10}$ or —$NR_{11}R_{12}$ where $R_{10}$, $R_{11}$ and $R_{12}$ each independently of one another represents hydrogen or a $C_1$ to $C_{20}$ hydrocarbon which can optionally contain one or more heteroatoms or one or more substituents, and Y in formula III represents O, S or Se and Y in formula VI represents O, S or $C(R)_2$.

4. The polycyclic dye as claimed in claim 3, wherein X represents —$NR_{11}R_{12}$.

5. The polycyclic dye as claimed in claim 4, wherein at least one of —$R_{11}$ and $R_{12}$ represents an alkyl or aryl substituted with —COOH.

6. The polycyclic dye as claimed in claim 3, wherein where $R_{13}$ represents hydrogen, aryl, carboxyphenyl, alkyl, perfluoroalkyl, cycloalkyl, pyridyl or carboxypyridyl.

* * * * *